US012085153B2

(12) United States Patent
Ahn et al.

(10) Patent No.: US 12,085,153 B2
(45) Date of Patent: Sep. 10, 2024

(54) ADJUSTABLE SPINAL PLATE

(71) Applicant: AEGIS SPINE, INC., Englewood, CO (US)

(72) Inventors: Youngbo Ahn, Englewood, CO (US); Sungak Choi, Englewood, CO (US); Sangsoo Lee, Englewood, CO (US); Geungrok Kim, Englewood, CO (US); Jongwon Hong, Englewood, CO (US)

(73) Assignee: AEGIS SPINE, INC., Englewood, CO (US)

( * ) Notice: Subject to any disclaimer, the term of this patent is extended or adjusted under 35 U.S.C. 154(b) by 204 days.

(21) Appl. No.: 17/963,339

(22) Filed: Oct. 11, 2022

(65) Prior Publication Data
US 2024/0117863 A1    Apr. 11, 2024

(51) Int. Cl.
*F16H 25/20* (2006.01)
*A61B 17/70* (2006.01)
*A61B 17/80* (2006.01)
*F16H 37/12* (2006.01)

(52) U.S. Cl.
CPC ......... *F16H 25/20* (2013.01); *A61B 17/7059* (2013.01); *A61B 17/8023* (2013.01); *F16H 37/124* (2013.01)

(58) Field of Classification Search
CPC .. F16H 25/20; A61B 17/7059; A61B 17/8023
See application file for complete search history.

(56) References Cited

U.S. PATENT DOCUMENTS

| | | | |
|---|---|---|---|
| 2002/0078529 A1* | 6/2002 | Schwarz | E05F 3/20 16/387 |
| 2013/0060283 A1 | 3/2013 | Suh et al. | |
| 2015/0230831 A1* | 8/2015 | Altarac | A61B 17/7058 606/246 |
| 2015/0336475 A1* | 11/2015 | Hoffmann | F16H 25/20 74/606 R |
| 2018/0110628 A1* | 4/2018 | Sharifi-Mehr | A61F 2/442 |
| 2018/0235671 A1* | 8/2018 | Jackson, III | A61B 17/7059 |
| 2024/0115297 A1* | 4/2024 | Ahn | A61B 17/7059 |

* cited by examiner

*Primary Examiner* — Tessa M Matthews
(74) *Attorney, Agent, or Firm* — WHDA, LLP

(57) ABSTRACT

The present invention provides a spinal plate which is used to perform fixation surgery on a spine in orthopedic surgery and neurosurgery. According to the present invention, a rotation device and a locking device may be installed so as to be used by fixing any one or more of longitudinal ends of the plate with being rotated at any angle, thereby allowing a doctor to modify a shape of the spinal plate to the shape desired by the doctor, and to perform the surgery by coping with various spin shapes of patients. In addition, according to the present invention, since the shape of the spinal plate may be rotated at any angle, it is possible to cope with various spin shapes of the patients.

6 Claims, 5 Drawing Sheets

ADJUSTABLE SPINAL PLATE

BACKGROUND OF THE INVENTION

1. Field of the Invention

The present invention relates to an adjustable spinal plate, and more specifically to a spinal plate which is used to perform fixation surgery on a spine in orthopedic surgery and neurosurgery.

2. Description of the Related Art

In general, a spine forms a pillar of the body, and an upper portion thereof is a portion forming a backbone of a human body that connects an upper skull and a lower pelvis. The spine includes 7 cervical vertebrae, 12 thoracic vertebrae, 5 lumbar vertebrae, 5 sacral vertebrae, and 3 to 5 coccyges from the top. In such a spine, symptoms such as an intervertebral disc disease and lumbar herniated intervertebral disc are likely to occur by prolonged or excessive use. In general, patients having spinal disorders such as spinal fracture and dislocation are subjected to treatment and correction by fixing the respective vertebrae so as not to be moved relative to each other. For this, a spinal fixation device has been widely used for fixing the vertebrae during fusion in the art.

Such a spinal plate generally refers to an implantation plate used for treatment of the spinal disorders. The spinal implant is used for spinal fusion in which a fusion cage of an artificial implant is inserted between vertebrae from which a damaged intervertebral disk is removed due to various spinal disorders, thus to restore and maintain an interval between the vertebrae. In the conventional case, the fusion cage inserted between the vertebrae is used simultaneously with bone screws and a rod applied simultaneously to the back of the vertebral body, or is used in such a manner in which the cage is coupled and fixed by a plate and connection bolts screwed to the vertebrae, or the cage itself is equipped with bone screw holes that can be installed the bone screws to directly fix the cage to the vertebrae.

However, since spin shapes are very diverse depending on conditions of the patients during the surgery, a case in which a doctor needs to use the spinal plate by modifying the shape thereof for each situation occurs. However, it is not easy to accurately modify the shape of the spinal plate according to the various spin shapes of the patients. Therefore, when actually performing the surgery, there are problems that the spinal plate does not adhere to the vertebrae but is detached or somewhat incompletely attached, thereby side effects occur or the surgery has to be performed again.

In addition, the patients prefer minimally invasive spine (MIS) surgery because of its potential benefits: less blood loss from surgery, reduced risk of muscle damage, reduced risk of infection and postoperative pain, faster recovery time, better cosmetic results because of relatively smaller skin incisions, etc. In order to perform MIS surgery, it is crucial that the doctors should be able to gain access to the spinal area by making as smaller skin incisions as possible and insert the spinal plate through these small skin incisions. In other words, the spinal plate, whose shape can be easily modified depending on conditions of the patients during the surgery and which can be inserted through patients' small skin incisions, is required for successful MIS surgery.

PRIOR ART DOCUMENT

Patent Document (Patent Document 1) U.S. Patent Application Publication No. US2018-0235671A (Patent Document 2) U.S. Patent Application Publication No. US2013-0060283A

SUMMARY OF THE INVENTION

An object of the present invention is to provide a spinal plate to be used by fixing any one or more of longitudinal ends of the plate with being rotated at any angle, thereby allowing a doctor to use the spinal plate by modifying a shape thereof to the shape desired by the doctor during a surgery, and to perform the surgery by coping with various spin shapes of patients.

In order to achieve the above object, according to an aspect of the present invention, there is provided An adjustable spinal plate comprising: a central body; and a pair of end bodies which are disposed on both sides of longitudinal direction of the central body and have one or more fixing screw holes in which fixing screws to be inserted into vertebrae are received, wherein at least one of the pair of end bodies includes a rotation device configured to fix the end body to the central body in a selectively rotatable manner, and a rotation locking device configured to maintain the rotation device in an unlocked state or a locked state, and the rotation lock device includes a switching unit that converts a rotational motion applying an external force into a linear motion, and a pressing unit that is displaced in the longitudinal direction of the central body by the switching unit and is in close contact with the rotation device to limit the rotation of the rotation device.

Herein a central joint is formed at both ends in the longitudinal direction of the center body, a wing fixing joint and a wing rotating joint are respectively formed in the wing body at positions corresponding to both ends of the central joint, the rotation device includes a joint rod rotatably penetrating the center joint and the wing rotating joint and non-rotatably penetrating the wing fixing joint, and a joint screw non-rotatably coupled to the joint rod and disposed through the central joint, the pressing unit is a worm block in contact with the helical surface of the thread part of the joint screw, and the switching unit is a rotation locking unit installed on the central body and of which the rotation radius of the outer peripheral surface is changed based on the rotation center by rotating while contacting the worm block in the opposite direction of the thread part.

In addition, the rotation locking unit includes a rotation locking unit shaft for rotating at a rotation locking unit seat of the central body, and a rotation locking unit head integrally connected to the rotation locking unit shaft, and the circumferential surface of the rotational locking unit head is provided with a rotational locking unit limiting part for applying the worm block so that the worm block is in close contact with the joint screw, and the rotation locking unit release portion that does not apply the worm block due to a shorter central radius than the central radius from the rotation center of the rotation locking unit limiting portion.

Further, a rotating locking unit marker is formed to protrude from the rotating locking unit head, and a rotating locking unit guide for constraining the rotational angle of the rotational locking unit marker is formed in the rotating locking unit seat of the central body.

Further, a wing sliding surface and a wing stopping surface in contact with the central supporting surface of the central body are continuously formed in the wing rotating joint and the wing fixing joint, the rotation of the wing body with respect to the central body is limited while the wing stopping surface is in surface contact with the central supporting surface.

Furthermore, a central sliding surface and a central stopping surface in contact with the wing support surface of the wing body are continuously formed in the central joint, and while the central stopping surface is in surface contact with the wing support surface, rotation of the wing body with respect to the central body is limited.

According to the present invention, the rotation device and the locking device may be installed so as to be used by fixing any one or more of longitudinal ends of the plate with being rotated at any angle, thereby allowing a doctor to modify a shape of the spinal plate to the shape desired by the doctor, and to perform the surgery by coping with various spin shapes of the patients.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, the present invention will be described in detail with reference to the accompanying drawings. In denoting reference numerals to constitutional elements of respective drawings, it should be noted that the same elements will be denoted by the same reference numerals although they are illustrated in different drawings. In the embodiments of the present invention, the publicly known functions and configurations that are judged to be able to make the purport of the present invention unnecessarily obscure will not be the present invention is not limited to the above-described specific embodiments and the modified examples, and it will be understood by those skilled in the related art that various modifications and variations may be made therein without departing from the scope of the present invention as defined by the appended claims.

In FIG. 1 to FIG. 2 and FIG. 10 to FIG. 12, reference numeral 100 designates an adjustable spinal plate according to an embodiment of the present invention.

Figure 1:
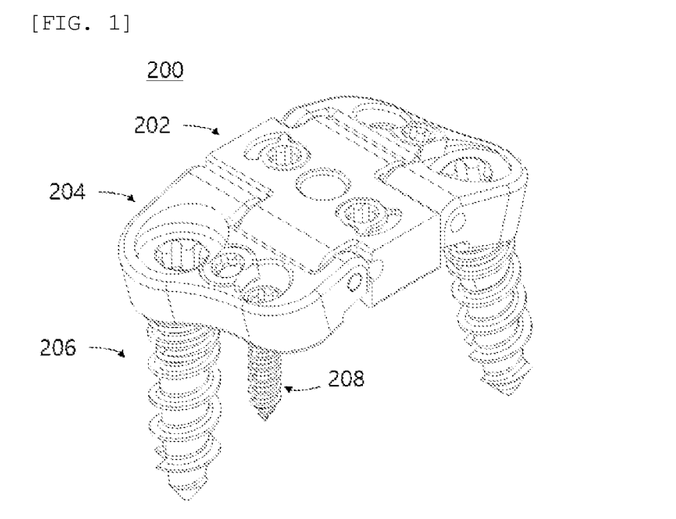
FIG. 1 is a perspective view illustrating an adjustable spinal plate according to embodiment of the present invention.
Figure 2:
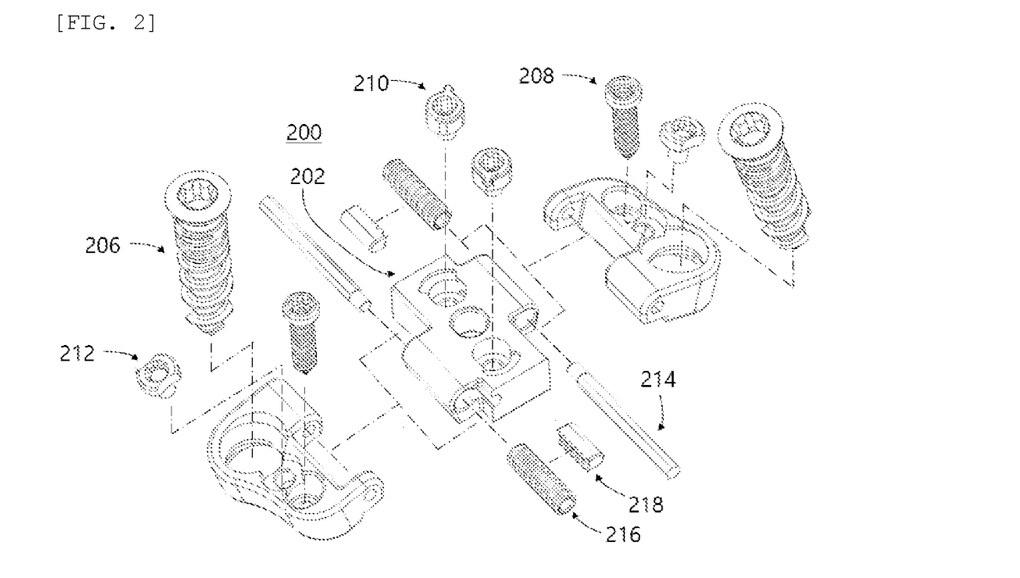
FIG. 2 is an exploded perspective view illustrating the adjustable spinal plate according to embodiment of the present invention.

The spinal plate 200 according to the present invention basically includes a central body 202, and a pair of wing bodies 204 in which one or more fixing screw hole 242 for accommodating the fixing screws 210 to be inserted into the spine are formed For explanation, the longitudinal direction of the central body 202 means a direction perpendicular to the width direction of the central body 202, and the pair of wing bodies 204 are connected to the central body 202 in the longitudinal direction of the central body 202.

Figure 3:
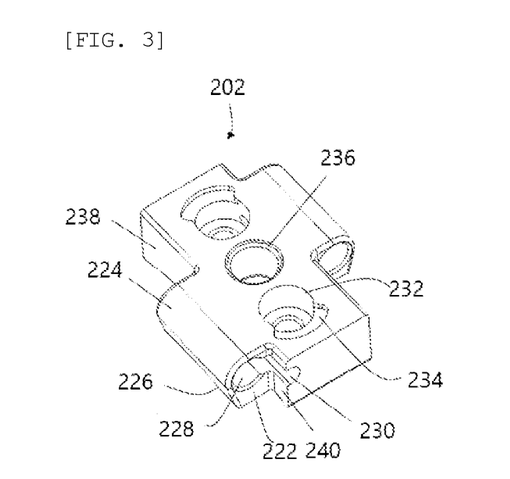
FIG. 3 is a perspective view illustrating a central body of the adjustable spinal plate according to embodiment of the present invention.
Figure 4:
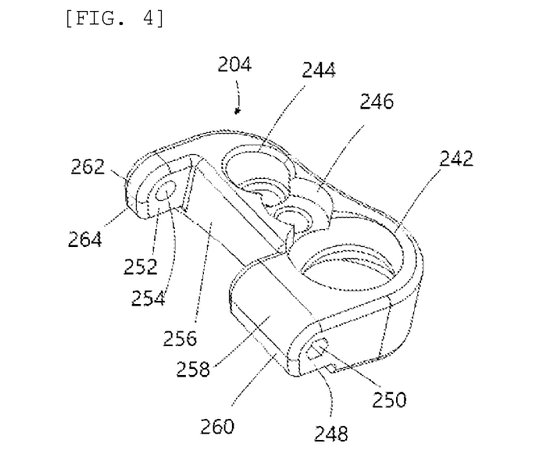
FIG. 4 is a perspective view illustrating a wing body of the adjustable spinal plate according to embodiment of the present invention.

As shown in FIG. 3, a central joint 222 is disposed at both ends of the central body 202 in the longitudinal direction, respectively. In addition, as shown in FIG. 4, the wing fixing joint 248 and the wing rotating joint 252 for connecting to the center joint 222 are disposed on the wing body 204. The coupling relationship between the center joint 222, the wing fixing joint 248, and the wing rotating joint 252 will be described again below.

As shown in FIG. 4, one or two fixing screw holes 242 may be disposed in one wing body 204, and as in the embodiment of the present invention an auxiliary screw hole 244 may be formed in the wing body 204 so that an auxiliary screw 208 smaller than the fixing screw 206 can be inserted.

After the fixing screw 206 and the auxiliary screw 208 are installed on the wing body 204, the screw locking unit 212 is installed so that the fixing screw 206 and the auxiliary screw 208 are not separated. It may be additionally installed on the wing body 204. A screw locking unit seat 246 in which the screw locking unit 212 is installed is disposed on the wing body 204.

Figure 6:
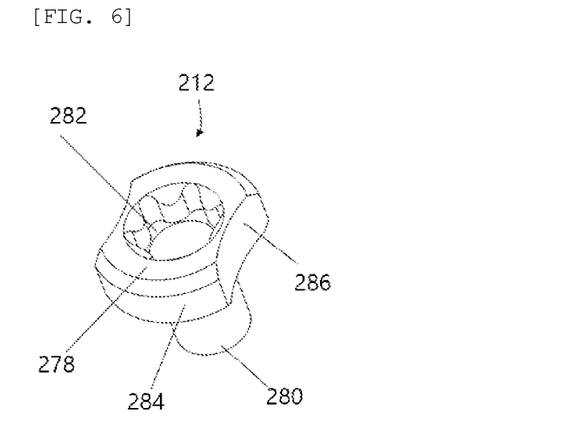
FIG. 6 is a perspective view illustrating a fixing screw locking unit of the adjustable spinal plate according to embodiment of the present invention.

As shown in FIG. 6, the screw locking unit 210 includes a screw locking unit shaft 280 to be inserted into the fixed screw locking unit seat 246, and a screw locking unit head 278 which is integrally formed with the screw locking unit shaft 280 and provided with a screw locking unit tool groove 282 connected to a tool for applying an external force.

A screw locking unit installation portion 286 formed to be concave is symmetrically disposed on a part of the circumference of the screw locking unit head 278, and a screw locking unit cover portion 284 formed convexly on the rest of the circumference is disposed. Accordingly, by rotating the screw locking unit 210, the fixing screw 206 and the auxiliary screw 208 can be inserted into the fixing screw hole 242 and the auxiliary screw hole 244, or in a state in which the fixing screw 206 and the auxiliary screw 208 are inserted, it is prevented from being separated from the fixing screw hole 242 and the auxiliary screw hole 244.

The pair of wing bodies 204 are fixed by a rotation device that connects to be rotatable with respect to the center body 202. In addition, a rotation locking device for maintaining the rotation device in an unlocked state or a locked state is connected to the rotation device so that the wing body 204 can be fixed at an arbitrary angle with respect to the central body 202.

The pair of wing bodies 104 are fixed by a rotation device so as to be rotatable with respect to the central body 102. In addition, the spinal plate 100 includes a rotation locking device for maintaining the rotation device in an unlocked state or a locked state so that the wing body 104 relative to the central body 102 can be fixed at an arbitrary angle.

The rotation locking device includes a switching unit for applying an external force, and a pressing unit in close contact with the rotation device by the switching unit to limit the rotation of the rotation device.

The switching unit applies a force to the pressing unit in the longitudinal direction of the central body 202 by rotation by an external force, and the pressing unit is displaced in the longitudinal direction of the central body 202 by the force of the shifting unit.

A center joint 222 is formed at both ends of the center body 202 in the longitudinal direction, and the wing body 204 has a wing fixing joint 248 and a wing rotating joint at positions corresponding to both ends of the central joint 222. The rotation device includes a joint rod 214 rotatably penetrating the central joint 222 and the wing rotating joint 252, a joint screw 216 non-rotatably coupled to the joint rod 214 and installed through the central joint 222.

In addition, the pressing unit is a worm block 218 in contact with the helical surface of a thread part 292 of the joint screw 216, and the switching part is a rotation locking unit 210 installed in the central body 202 in which the rotation radius of the outer circumferential surface is changed based on the rotation center by rotating while in contact with the worm block 218 in the opposite direction to the thread part 292.

Figure 7:
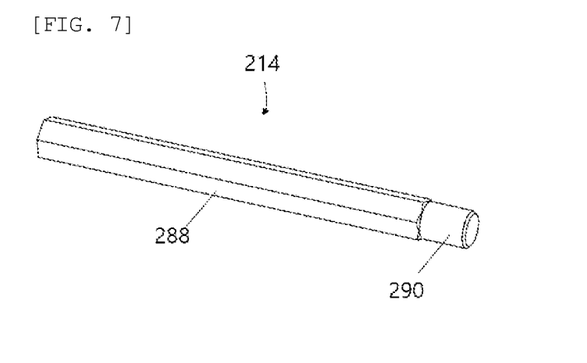
FIG. 7 is a perspective view illustrating a joint rod of the adjustable spinal plate according to embodiment of the present invention.

As shown in FIG. 7, the joint rod 214 includes a rod fixing part 288 and a rod rotating part 290. The rod fixing part 288 may be connected in a non-rotatable state with respect to the joint screw 216 or the wing fixing joint 248 by having a polygonal cross section. In the embodiment of the present invention, the rod fixing part 288 has a regular hexagonal cross section, and it is also possible to have a cross section of another shape. Similarly, the wing rod fixing hole 250 of the wing fixing joint 248 also has a cross section of the same shape as that of the rod fixing part 288. In addition, the rod insertion hole 294 of the joint screw 216 into which the joint rod 214 is inserted has the same cross section as that of the rod fixing part 288.

In addition, the rod rotating part 290 has a circular cross section, and is installed to be rotatable relative to the wing rotating joint 252. Accordingly, the wing rotating joint 252 is formed with a wing rod rotating hole 254 having the same cross section as the rod rotating part 290.

Figure 5:
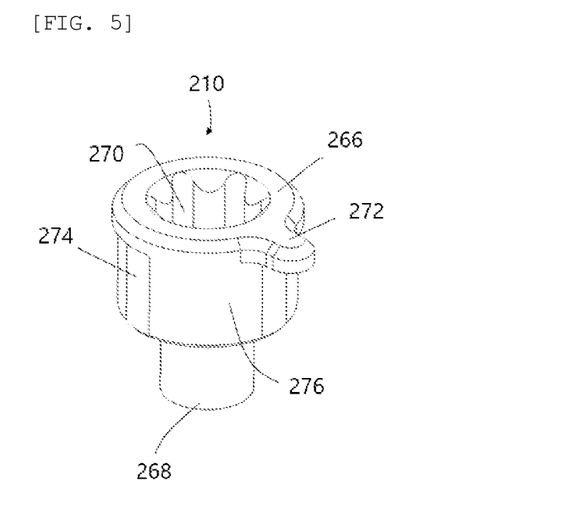
FIG. 5 is a perspective view illustrating a rotating locking unit of the adjustable spinal plate according to embodiment of the present invention.

As shown in FIG. 5, the rotating locking unit 210 includes a rotation locking unit shaft 268 for rotating at the rotating locking unit seat 232 of the central body 202, and a rotating locking unit head 266 integrally connected to the rotation locking unit shaft 268. A rotating locking unit limiting portion 276 for attaching the worm block 218 so that the worm block 218 is in close contact with the joint screw 216, and a rotating locking unit release portion 274 that does not apply the worm block 218 because the central radius from the rotation center of the rotating locking unit shaft 268 is shorter than that of the rotating locking unit limiting portion 276 are formed in the circumferential surface of the rotating locking unit head 266.

The rotating locking unit limiting portion 276 and the rotating locking unit releasing portion 274 formed on the rotating locking unit head 266 serve as a cam. Accordingly, a transition portion may be formed between the rotating locking unit limiting portion 276 and the rotating locking unit releasing portion 274 to gradually push the worm block 218.

Figure 8:
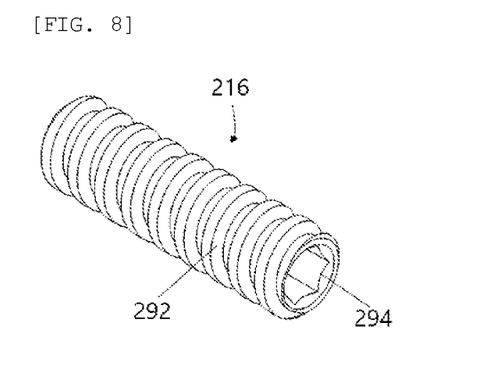
FIG. 8 is a perspective view illustrating a joint screw of the adjustable spinal plate according to embodiment of the present invention.

In addition, a rotation locking unit marker 272 is formed to protrude from the rotating locking unit head 266, and A rotation locking unit guide 234 that restricts the rotation angle of the rotating locking unit marker 272 is formed in the rotating locking unit seat 232 of the central body 202. The rotating locking unit guide 234 is an arc-shaped groove, and since the rotating locking unit marker 272 can move only within the rotating locking unit guide 234, the rotation angle of the rotating locking unit 210 can be limited As shown in FIG. 8, the joint screw 216 is formed with a thread part 292 having a screw thread on the outer peripheral surface. In addition, rod insertion hole 294 into which the rod fixing part 288 of the joint screw 216 is inserted is formed in the joint screw 216.

Figure 9:
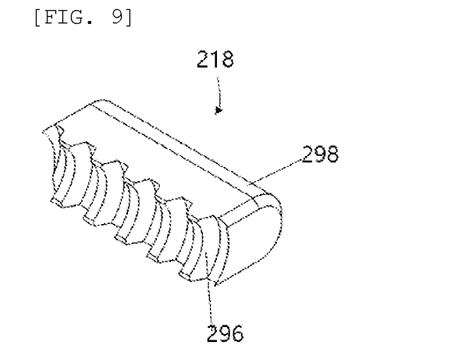
FIG. 9 is a perspective view illustrating a worm block of the adjustable spinal plate according to embodiment of the present invention.

In addition, as shown in FIG. 9, the worm block 218 includes a thread contacting part 296 having a shape that can be in contact with the thread part 292 of the joint screw 216, and a rotating locking unit contacting part 298 in contact with the outer circumferential surface of the screw locking unit head 278 in the opposite side.

The worm block 218 is located at the worm block seat 230 formed on the central body 202, and has a margin that allows movement in the width direction of the central body 202 only to ½ of the screw pitch of the thread part 292. Even if the position of the thread contacting part 296 and the thread part 292 of the worm block 218 is slightly shifted from each other, the thread contacting part 296 and the thread part 292 can be coupled to each other by the margin.

The thread contacting part 296 has a partial spiral shape capable of directly contacting the thread surface of the thread part 292. Accordingly, when the worm block 218 comes into contact with the joint screw 216 and is applied with force, the joint screw 216 and the worm block 218 are coupled like a worm and a worm gear. Accordingly, rotation of the joint screw 216 can be prevented by the contact of the worm block 218 with the joint screw 216. Additionally, even if the joint screw 216 tries to rotate even a little due to disturbance in a state in which the rotation of the joint screw 216 is prevented, the worm block 218 cannot move in the center of the worm block seat 230 in the width direction of the body 202 so that the rotation prevention state can be maintained.

Figure 10:
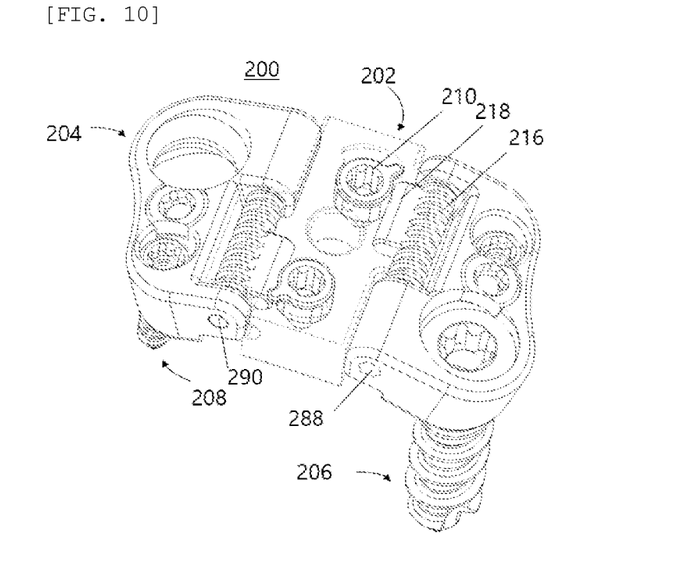
FIG. 10 is a partially penetrating perspective view illustrating a locking mechanism used in the adjustable spinal plate according to embodiment of the present invention.
Figure 11:
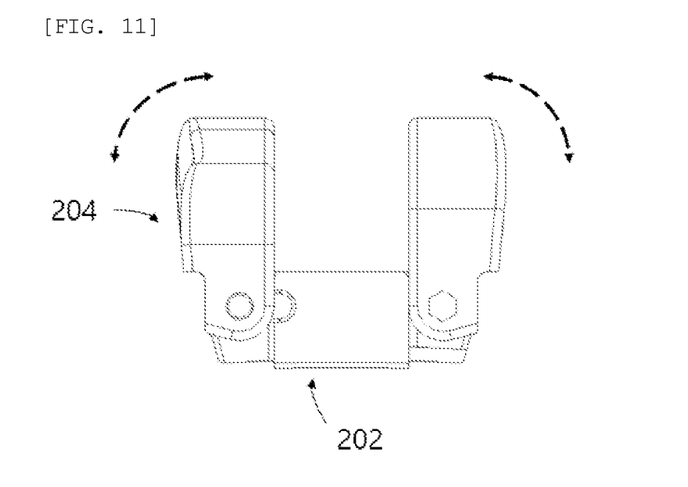
FIG. 11 is a side view illustrating a state in which the adjustable spinal plate according to embodiment of the present invention is being inserted with being folded.
Figure 12:
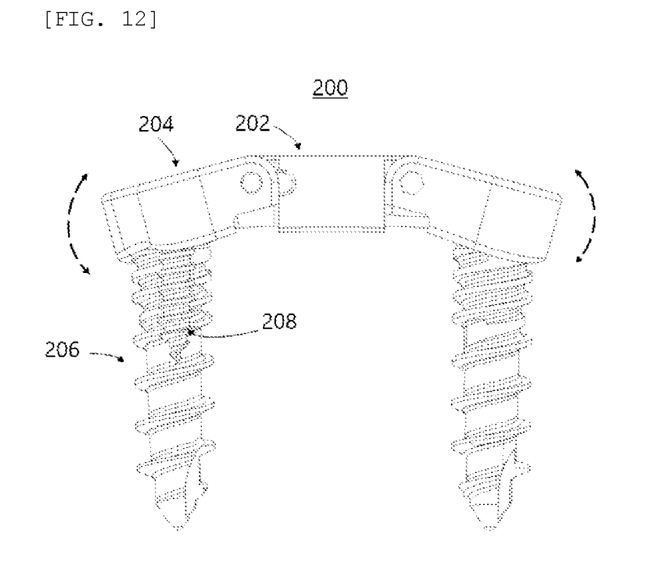
FIG. 12 is a side view illustrating a state in which the adjustable spinal plate according to embodiment of the present invention has been inserted with being unfolded.

Since the rotating locking unit 210 does not apply the worm block 218 in the unlocked state, the joint screw 216 which is positioned inside the central joint 222 by the joint rod 214 is free to rotate. As a result, since the joint rod 214 fixed only to the wing fixing joint 248 is in a rotatable state with the wing rotating joint 252, the wing body 204 is the center body 202 is relatively rotatable. This state is the unlocked state.

When the rotating locking unit 210 is rotated by a tool, the rotating locking unit marker 272 can be rotated to a maximum angle allowed by the rotating locking unit guide 234, and at this time, as the rotating locking unit limiting portion 276 of the rotating locking unit head 266 comes into contact with the rotating locking unit contacting part 298, the worm block 218 is applied by force.

As a result, the worm block 218 comes into contact with the joint screw 216 while displaced in the longitudinal direction of the central body 202, thereby preventing the joint screw 216 from rotating. Since the joint rod 214, which rotates integrally with the joint screw 216, is also prevented from rotating, the wing body 204 is in a locked state in which rotation is prevented relative to the central body 202.

Therefore, when the user rotates the rotation locking unit 210 in a state where the wing body 204 is set at an arbitrary angle with respect to the central body 202, it is possible to fix the wing body 204 at any angle with respect to the central body 202.

It is preferable that the angle at which the wing body 204 is rotated is limited to the lower side than the straight line in the longitudinal direction of the central body 202 in order to correspond to the structure of the spine of the human body.

In order to implement this, the wing rotating joint 252 and the wing fixing joint 248 have wing sliding surfaces 258, 262 and wing stopping surfaces 260, 264 which are formed continuously in contact with the central supporting surfaces 238, 240 of the central body 202. While the wing stopping surfaces 260, 264 are in surface contact with the central supporting surfaces 238, 240, the rotation of the wing body 204 with respect to the center body 202 may be limited. The wing sliding surfaces 258, 262 are disposed on the upper side of the wing rotating joint 252 and the wing fixing joint 248, and the wing stopping surfaces 260, 264 are disposed on the lower side of the rotation joint 252 and the wing fixing joint 254 in succession to the wing sliding surfaces 258, 262.

In addition, the center joint 222 has a central sliding surface 224 and a central stopping surface 226 which are formed continuously in contact with the wing support surface 256 of the wing body 204. While the central stopping surface 226 are in surface contact with the wing support surface 256, the rotation of the wing body 204 with respect to the center body 202 may be limited. The central sliding surface 224 is disposed on the upper side of the central joint 222, and the central stopping surface 226 are disposed on the lower side of the central joint 222 in succession to the central sliding surface 224.

That is, the wing sliding surfaces 258, 262 or the central sliding surface 224 are in line contact with the central supporting surfaces 238, 240 and the wing supporting surface 256, respectively, but the wing stopping surfaces 260, 264 or the central stopping surface makes surface contact with the central supporting surfaces 238, 240 and the wing supporting surface 256, respectively. As a result, the rotation of the wing body 204 with respect to the center body 202 can be limited.

The rotation limiting angle of the wing body 204 with respect to the center body 202 may be changed according to the intention of the designer.

While the present invention has been described with reference to the preferred embodiments and modified examples, the present invention is not limited to the above-described specific embodiments and the modified examples, and it will be understood by those skilled in the related art that various modifications and variations may be made therein without departing from the scope of the present invention as defined by the appended claims.

According to the present invention, it is possible to use the spinal plate by modifying the shape thereof in the shape desired by the doctor during the surgery, thereby developing a spinal plate that can cope with the various spin shapes of the patients.

In addition, the shape of the spinal plate may be deformed at various angles with a single plate, it is possible to reduce the burden of preparing the plates for each operation during the surgery, thereby greatly reducing product costs from the manufacturer's point of view.

DESCRIPTION OF REFERENCE NUMERALS

200: Spinal plate
202: Central body
204: Wing body
206: Fixing screw
208: Auxiliary screw
210: Rotating locking unit
212: Screw locking unit
214: Joint rod
216: Joint screw
218: Worm block
222: Central joint
224: Central sliding surface
226: Central stopping surface
228: Central rotating pin hole
230: Worm block seat
232: Rotating locking unit seat
234: Rotating locking unit limiting part
238, 240: Central supporting surface
242: Fixing screw hole
244: Auxiliary screw hole
246: Screw locking unit seat
248: Wing fixing joint
250: Wing rod fixing hole
252: Wing rotating joint
254: Wing rod rotating hole
256: Wing supporting surface
258, 262: Wing sliding surface
260, 264: Wing stopping surface
266: Rotating locking unit head
268: Rotating locking unit shaft
270: Rotating locking unit tool groove
272: Rotating locking unit tool guide
274: Rotating locking unit releasing portion
276: Rotating locking unit pressing portion
278: Screw locking unit head
280: Screw locking unit shaft
282: Screw locking unit tool groove
284: Screw locking unit cover part
286: Screw locking unit insertion part
288: Rod fixing part
290: Rod rotating part
292: Thread part
294: Rod insertion hole
296: Thread contacting part
298: Rotating locking unit contacting part

What is claimed is:

1. An adjustable spinal plate comprising:
a central body; and
a pair of end bodies which are disposed on both sides of a longitudinal direction of the central body and have one or more fixing screw holes in which fixing screws to be inserted into vertebrae are received,
wherein at least one of the pair of end bodies includes a rotation device configured to fix the end body to the central body in a selectively rotatable manner, and a rotation locking device configured to maintain the rotation device in an unlocked state or a locked state, and
the rotation locking device includes a switching unit that converts a rotational motion applying an external force into a linear motion, and a pressing unit that is displaced in the longitudinal direction of the central body by the switching unit and is in close contact with the rotation device to limit the rotation of the rotation device.

2. The adjustable spinal plate according to claim 1, wherein a central joint is formed at both ends in the longitudinal direction of the center body, a wing fixing joint and a wing rotating joint are respectively formed in a wing body at positions corresponding to both ends of the central joint, the rotation device includes a joint rod rotatably penetrating the center joint and the wing rotating joint and non-rotatably penetrating the wing fixing joint, and a joint screw non-rotatably coupled to the joint rod and disposed through the central joint, the pressing unit is a worm block in contact with a helical surface of a thread part of the joint screw, and the switching unit is a rotation locking unit installed on the central body and of which a rotation radius of an outer peripheral surface is changed based on a rotation center by rotating while contacting the worm block in the opposite direction of the thread part.

3. The adjustable spinal plate according to claim 2, wherein the rotation locking unit includes a rotation locking unit shaft for rotating at a rotating locking unit seat of the central body, and a rotating locking unit head integrally connected to the rotation locking unit shaft, and a circumferential surface of the rotating locking unit head is provided with a rotational locking unit limiting part for applying the worm block so that the worm block is in close contact with the joint screw, and a rotation locking unit release portion that does not apply the worm block due to a shorter central radius than a central radius from the rotation center of the rotation locking unit limiting part.

4. The adjustable spinal plate according to claim 3, wherein a rotating locking unit marker is formed to protrude from the rotating locking unit head, and a rotating locking unit guide for constraining a rotational angle of the rotating locking unit marker is formed in the rotating locking unit seat of the central body.

5. The adjustable spinal plate according to claim 2, wherein a wing sliding surface and a wing stopping surface in contact with a central supporting surface of the central body are continuously formed in the wing rotating joint and the wing fixing joint, the rotation of the wing body with respect to the central body is limited while the wing stopping surface is in surface contact with the central supporting surface.

6. The adjustable spinal plate according to claim 2, wherein a central sliding surface and a central stopping surface in contact with a wing support surface of the wing body are continuously formed in the central joint, and while the central stopping surface is in surface contact with the wing support surface, rotation of the wing body with respect to the central body is limited.

* * * * *